(12) United States Patent  
Sparrman et al.

(10) Patent No.: US 11,192,810 B2  
(45) Date of Patent: Dec. 7, 2021

(54) WASTE TREATMENT SYSTEMS AND METHODS

(71) Applicant: Greywater Industries, LLC, Gulfport, MS (US)

(72) Inventors: Jan Olov Sparrman, Gulfport, MS (US); Chris van Son, Gulfport, MS (US); Eric d'Arcy, Gulfport, MS (US)

(73) Assignee: GREYWATER INDUSTRIES, LLC, Gulfport, MS (US)

( * ) Notice: Subject to any disclaimer, the term of this patent is extended or adjusted under 35 U.S.C. 154(b) by 0 days.

(21) Appl. No.: 16/520,455

(22) Filed: Jul. 24, 2019

(65) Prior Publication Data

US 2019/0345048 A1   Nov. 14, 2019

Related U.S. Application Data

(63) Continuation of application No. PCT/US2018/016367, filed on Feb. 1, 2018.
(Continued)

(51) Int. Cl.
*C02F 3/06* (2006.01)
*C02F 9/00* (2006.01)
(Continued)

(52) U.S. Cl.
CPC .......... *C02F 3/06* (2013.01); *C02F 3/341* (2013.01); *C02F 9/00* (2013.01); *C02F 2101/16* (2013.01);
(Continued)

(58) Field of Classification Search
CPC .... C02F 2103/20; C02F 3/30; C02F 2101/16; C02F 2101/163; C02F 2101/166;
(Continued)

(56) References Cited

U.S. PATENT DOCUMENTS 4,675,144 A   6/1987  Hammond  
5,120,435 A *  6/1992  Fink .................. B01D 17/00  
                                              210/192  
(Continued)

FOREIGN PATENT DOCUMENTS

WO    1998050311 A1    11/1998  
WO    2015054783 A1     4/2015

OTHER PUBLICATIONS

ISA/RU, International Search Report for International Patent Application No. PCT/US 2018/016367, dated Jun. 14, 2018, 4 pages.
ISA/RU, Written Opinion of the International Searching Authority for International Patent Application No. PCT/US 2018/016367, dated Jun. 14, 2018, 5 pages.
WIPO, International Preliminary Report on Patentability for International Patent Application No. PCT/US 2018/016367, dated Aug. 6, 2019, 6 pages.
(Continued)

*Primary Examiner* — Claire A Norris  
(74) *Attorney, Agent, or Firm* — NK Patent Law

(57) ABSTRACT

A method for obtaining grey water excreta includes reducing ammonia content of the liquid fraction in a first porous medium in which the ammonia content is decomposed, and reducing the byproducts in a second batch of similar porous medium. The byproduct may be decomposed into nitrogen. A system for obtaining grey water from a liquid fraction of human or animal excreta includes: a first bio-filter for reducing an ammonia content of the liquid fraction, the first bio-filter including a first vessel and a first porous medium in which the ammonia content is at least in part decomposed into at least one byproduct; and a second bio-filter for reducing the at least one byproduct, the second bio-filter including a second vessel and a second batch of similar porous medium within the second vessel and in which the at least one byproduct is at least in part decomposed.

20 Claims, 2 Drawing Sheets

Related U.S. Application Data

(60) Provisional application No. 62/453,642, filed on Feb. 2, 2017.

(51) Int. Cl.
  *C02F 3/34* (2006.01)
  *C02F 101/16* (2006.01)
  *C02F 101/20* (2006.01)
  *C02F 103/20* (2006.01)

(52) U.S. Cl.
  CPC ...... *C02F 2101/20* (2013.01); *C02F 2103/20* (2013.01)

(58) Field of Classification Search
  CPC .......... C02F 3/06; C02F 3/2806; C02F 3/302; C02F 3/303; C02F 3/305; C02F 9/00; C02F 3/341
  USPC ................................................. 210/615, 620
  See application file for complete search history.

(56) References Cited

U.S. PATENT DOCUMENTS

| | | | | |
|---|---|---|---|---|
| 6,387,267 | B1* | 5/2002 | Kantardjieff | C02F 11/004 210/615 |
| 2004/0251198 | A1* | 12/2004 | Lord | C02F 3/1215 210/615 |
| 2011/0011800 | A1* | 1/2011 | Cord-Ruwisch | C02F 3/06 210/620 |
| 2015/0040628 | A1* | 2/2015 | Parrish | C05D 9/00 71/22 |

OTHER PUBLICATIONS

Hegger. Kyle Joseph, "Wastewater Treatment by Novel Hybrid Biological—Ion Exchange Processes", Thesis—University of Illinois at Urbana-Champaign, 2010, 21 pages.

\* cited by examiner

WASTE TREATMENT SYSTEMS AND METHODS

CROSS-REFERENCE TO RELATED APPLICATIONS

This application is a continuation of International Patent Application No. PCT/US18/16367, titled "WASTE TREATMENT SYSTEMS AND METHODS," filed on Feb. 1, 2018, which claims the benefit of U.S. Provisional Patent Application No. 62/453,642, titled "WASTE WATER TREATMENT SYSTEMS AND METHODS," filed on Feb. 2, 2017, the entire contents of which are all hereby incorporated herein by reference.

TECHNICAL FIELD

The present disclosure relates to waste treatment systems and methods. More particularly, the present disclosure relates to systems and methods for obtaining grey water from a liquid fraction of human or animal feces, and growing a microbic culture for us in treating the liquid fraction.

BACKGROUND

In a typical livestock farm, manure is stored under the floor of a stable or in open lagoons nearby. Farmers have to manage this manure either by using it as a fertilizer or by transporting it to centralized storing places for further transport to land where the manure can be spread over the land or injected in the soil. In some countries, farmers are limited in the number of animals they manage in relation to the size of the available land for spreading or injection of animal wastes.

The sheer quantities of manure can cause environmental problems, inconvenience and danger to people and/or animals too close to waste lagoons. Human and animal feces have relatively high water content. The relatively high ammonia content of the liquid fraction of feces is also a concern.

Existing natural biological filtration processes are insufficient in reducing ammonia content to an extent that the purified grey water can be discharged. Existing alternative filtration processes are typically too laborious or cost-intensive to make obtaining grey water from feces worthwhile. Biological filtration processes for purifying contaminated water, water mixtures and other liquid fractions varying in nature are known as such. But there are no satisfactory existing systems or methods for the treatment of the liquid fraction of animal waste. Increasingly, government institutions, such as the Environmental Protection Agency of the United States, are implementing or approaching oversight or regulatory requirements for waste management programs for livestock such as swine.

Solutions are needed to manage these problems and to reliably assure regulatory compliance. Farmers need a solution for treatment of manure, and system in which the liquid fraction of animal waste can be separated from the solid fraction.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

In at least one embodiment, a method for obtaining grey water from a liquid fraction of human or animal feces includes: containing and purifying the liquid fraction using a biological filtration process; and reducing the ammonia content of the liquid fraction using bio-filters where a microbic culture is present on porous granules.

The porous granules may be placed in a bio-filter unit into which the liquid fraction is provided after containing in a collecting tank.

The liquid fraction may be mixed with the porous granules by pumping the liquid fraction from the collecting tank to the bio-filter unit.

The mixture may be aerated by pumping an airflow into the bio-filter unit.

Prior to providing the liquid fraction to the bio-filter with the porous granules, the porous granules may have undergone a culturing process of the growth of a microbic culture on the porous granules.

A small quantity of the liquid fraction to be processed may be mixed with the porous granules during the culturing process in order to match said microbic culture to grow with the feces to be processed.

Biological decomposition of ammonia may be provided by at least one biological process selected from a group consisting of an aerobe biological process and an anaerobe biological process.

The microbic culture may contain at least one bacterium selected from the group consisting of nitrosomonas and nitrobacteria.

The porous granules may be selected from a group consisting of granules of volcanic rock, or zeolite of the clinoptilolite or the mordenite group. The porous granules may be porous ceramic granules.

The porous granules may have a particle size with an average diameter ranging from 10 mm and 30 mm.

In at least one embodiment, a housing accommodates porous granules, to mix the liquid fraction with the porous granules and for aerating in order to stimulate microbic growth in a microbic culture present on the granules, all for the biological decomposition of ammonia in the liquid fraction.

The liquid fraction may be pumped from the collecting tank into the bio-filter unit for mixing the liquid fraction with the porous granules.

In at least one embodiment, a microbic culture is grown on porous granules, for use in a method according to any of the above examples and embodiments. The porous granules are mixed with a small quantity of a liquid fraction of human or animal feces; and the porous granules and the liquid fraction are aerated for growing the microbic culture on said porous granules.

In at least one embodiment a method for obtaining grey water from a liquid fraction of human or animal excreta includes: reducing an ammonia content of the liquid fraction in a first porous medium in which the ammonia content is at least in part decomposed into at least one byproduct; and reducing the at least one byproduct in a second porous medium in which the at least one byproduct is at least in part decomposed into nitrogen.

In at least one embodiment, a system for obtaining grey water from a liquid fraction of human or animal excreta includes a first bio-filter for reducing an ammonia content of the liquid fraction. The first bio-filter includes a first vessel and a first porous medium in which the ammonia content is at least in part decomposed into at least one byproduct. A second bio-filter reduces the byproduct. The second bio-filter includes a second vessel and a second similar porous medium. The byproduct may be decomposed into nitrogen.

The system may include a pressure filter subsystem including a pump that pumps liquid from the second bio-filter, via a collecting tank to a set of filter tanks. The pressure filter subsystem may include a second filter tank and at least one conduit through all the filter tanks.

The first porous medium may include granules of a first mineral; and the second porous medium may include granules of a similar mineral. The minerals may include a zeolite.

Reducing the ammonia content of the liquid fraction by an aerobic biological process and reducing at least one byproduct of the liquid fraction in an anaerobic biological process may include using bacteria from the nitrosomonas and nitrobacteria families.

After reducing the ammonia content of the liquid fraction, filtering the liquid fraction may remove particles larger than a predetermined size. Removing particles larger than a predetermined size may include removing particles larger than one micrometer. Removing particles may include removing bacteria.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

Figure 1:
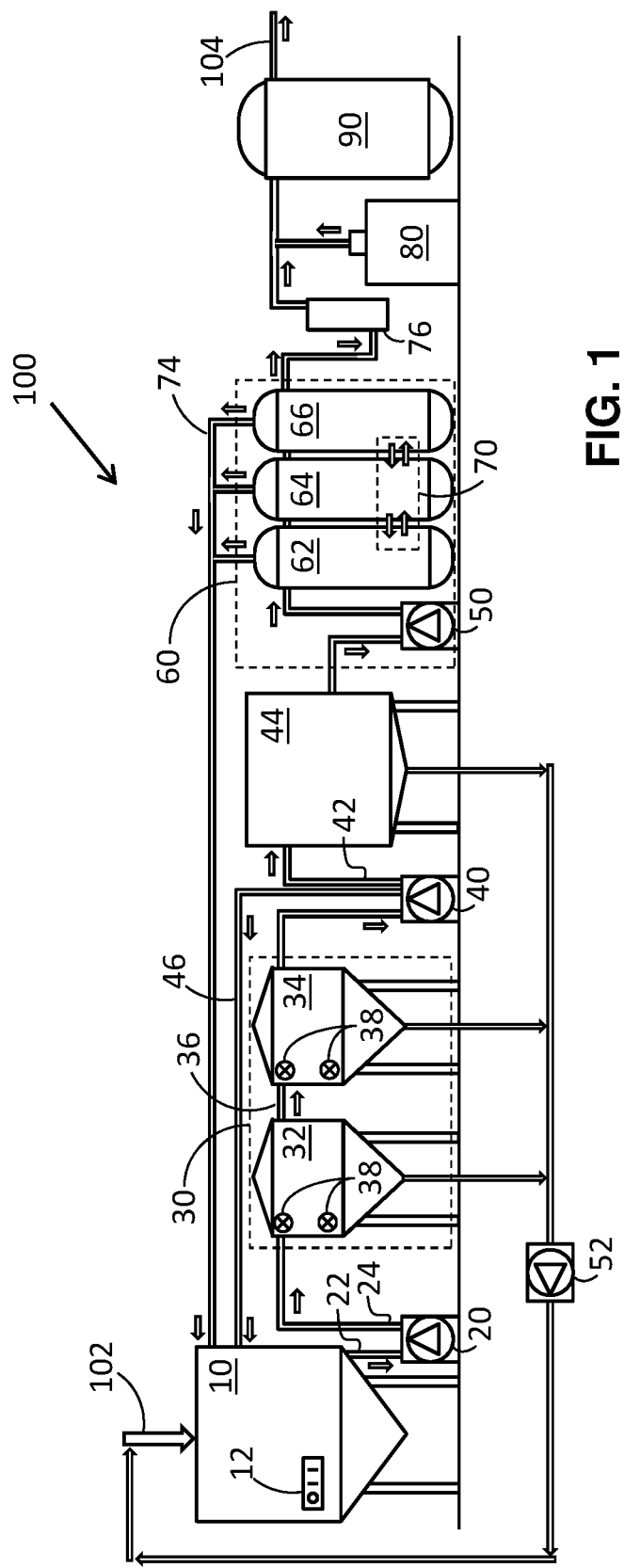
FIG. 1 is a diagrammatic representation of a system for obtaining grey water from a liquid fraction of human or animal feces according to at least one embodiment.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings.

A biological filtration method described hereafter makes it possible, after separation of liquid and solid fractions of animal waste, to purify and process the liquid fraction into grey water that can be discharged in open water in accordance with the existing environmental standards. Grey water is obtained from a liquid fraction of human or animal feces, by use of bio-filter units, storage tanks, and by treatment of the liquid by use of a microbic culture grown for this use.

The solid fraction can be used as fertilizer, production of bio-gas, and pellets for energy production. The solid fraction has most of the phosphate content in the manure. The liquid fraction can be treated along the process described here.

Upstream of the illustrated sections of the system 100 of FIG. 1, animal excreta, referring to feces and possibly urine therewith, are separated into waste solids and liquid fractions. For example, a variety of decanters, centrifuges and drum filters may be utilized, or other techniques may be used. It is preferable to remove solids (particles) down to a size of 50-100 micron. The liquid fraction is then pumped to the treatment system 100 or delivered in a container.

In the system 100, incoming liquid waste 102 is collected in a collection and settling tank 10 where settling of any particles takes place. For example, settling time may be about 1 hour. Other settling times are within the scope of these descriptions. The collection and settling tank 10 in at least one example, as illustrated in FIG. 1, is equipped with a collecting conical bottom, for the settled sediment. The collection and settling tank 10 may have a man hole for entry, cleaning and service. The tank may have passive or forced ventilation, level-metering, and a controller 12 for starting and stopping operations. The collection and settling tank 10 may also have alarm and recirculation devices. The controller 12 may further control downstream devices and subsystems of the system 100. In some embodiments, the other devices and subsystems have additional controllers such as the controller 12 shown for the collection and setting tank 10 in FIG. 1.

At the collection and settling tank 10, after settling occurs, the collected liquid is passed by a pump 20 and intermediary conduits 22 and 24 from the collection and settling tank 10 to a bio-filter subsystem 30, which is illustrated in FIG. 1 as a staged system having two bio-filters 32 and 34, illustrated in series arrangement although parallel arrangement as possible as well. Other embodiments of the bio-filter subsystem 30 within the scope of these descriptions can have any number of staged bio-filters.

In at least one embodiment, the bio-filters 32 and 34 are specially designed for the system 100. In at least one example, the bio-filters 32 and 34 are constructed as sequentially arranged vessels in fluid communication via an intermediary conduit 36. The vessels are filled with process facilitating materials or mediums, for example selected natural stones of a volcanic mineral fragmented into porous granules. The medium may be a mineral, such as a zeolite, preferably of the clinoptilolite group (such as Aqualite™) with the advantageous structure of an enormous active area of up to 500 meters squared ($m^2$) per gram, thus being an excellent carrier or host for biological processes such as the growth of microbes.

In the bio-filters 32 and 34 a microbic (bacterial) culture has been initiated and, with a flow of air, grown. A small quantity of the liquid fraction to be processed by the bio-filter subsystem 30 can be mixed with the porous granules for preliminary microbic culturing prior to initiating full processing by the system 100. Such preliminary culturing advantageously matches the microbic culture to grow with the animal waste to be processed.

The biological decomposition of ammonia is effected in the bio-filters 32 and 34 by use of at least one selected biological process. An aerobic biological process, an anaerobic biological process, or both such processes may be utilized. In at least one embodiment, an aerobic biological process is promoted in the first stage bio-filter 32, which can be effected for example by using bacteria of the nitrosomonas family. An anaerobic process can be effected, in the second stage bio-filter 34 by using bacteria of the nitrobacter family. The aerobic process in bio-filter 32 will initially ensure that ammonia is converted into nitrates and nitrites, while the anaerobic process in bio-filter 34 will subsequently ensure that the nitrates and nitrites are decomposed to release nitrogen gas.

The bio-filters 32 and 34 may each have an aeration level, and can be used separately or together. The illustrated arrangement allows for alternative biological processes such as aerobe and anaerobe processes by adjusting the aerations in each bio-filter independently of the other.

The bio-filters 32 and 34 are designed for controllable aeration for the bio processes and include air pressure for backwashing and sludge emptying. Depending on the manure and the separation solids and liquids, backwashing may take place periodically or upon need. For example, periodic backwashing may be conducted once a day or once a week and may take between 2 and 10 minutes.

In at least one embodiment, each bio-filter 32 and 34 has two aeration supply elements 38, which may be compressors or air lines for example, one of which is used for aeration and the other of which is used for backwashing, Backwashing of either bio-filter can be managed by using a lower aeration nozzle or aeration supply element 38 with increased pressure. More or less than two aeration supply elements may be used with each bio-filter. The system 100 provides conduits and valves to connect the two bio-filters 32 and 34 in parallel with the option to connect them in serial configuration, as shown in FIG. 1, depending on the liquid content and outlet demand.

The liquid effluent from the bio-filter subsystem 30 can also be recirculated back to the collection and settling tank 10 if needed, for example when no liquid comes from the separation step. When a level control in the collection and settling tank 10 gives a signal to prompt recirculation, liquid will be recirculated from the bio-filter subsystem 30 to the collection and settling tank 10 until a control switch gives a start signal for the standard program, for example at the controller 12. A pump 40 and one more valves can direct processed liquid from the bio-filter subsystem 30 downstream to a collecting tank 44 via a conduit 42 or from the bio-filter subsystem back to the collection and settling tank 10 for recycling via conduit 46.

After the biological processes of the bio-filter subsystem 30, further downstream processing of the liquid effluent from the bio-filter subsystem 30 is taken to the downstream collecting tank 44, which is equipped with a level switch as well as start, stop, and alarm devices. A pump 50 pumps the liquid to a staged pressure filter subsystem 60 for final treatment via intermediary conduits.

A pump 52 and connecting conduits optionally route or recirculate, for example back to the collection and settling tank 10, any of the liquid from outputs of the collection and settling tank 10, the bio-filter subsystem 30 (bio-filters 32 and 34) and collecting tank 44.

Continuing with further downstream processing, the staged pressure filter subsystem 60 can include any number of pressure filter tanks. The pressure filter subsystem 60 is represented in FIG. 1 as having the pump 50 and three pressure filter tanks 62, 64, 66 arranged for sequential process filtering. The system 100 provides conduits and valves to connect the pressure filter tanks in parallel with the option to connect them in serial configuration. The pressure filter subsystem 60 in at least one embodiment has four or more pressure filter tanks. In one such embodiment, the pressure filter tanks are connected as two groups in parallel in one configuration, and in serial in another configuration. The pressure filter tanks 62, 64, 66, in any number, may be filled with the same volcanic mineral granules as used in the bio-filters 32 and 34 of the bio-filter subsystem 30, or other materials.

The pressure filter subsystem 60 removes particles down to a size of 1 micron. For example, bacteria can be removed by about 90-98% by filtering, heavy metals and ammonia by ion-exchanging, oil and fats by adsorption. The pressure filter tanks of can be backwashed and regenerated if necessary. They are inter-connected, for example via conduits 70 as represented in FIG. 1, so that one filter can be backwashed by using liquid from one or more of the others, which eliminates or reduces the need of separate reservoirs and pumps for backwashing. Backwashing may be conducted periodically or upon need. For example, backwashing daily may take 2-5 minutes for each pressure filter tank. A recycling conduit set 74 may be provided to recycle liquids from the pressure filter subsystem 60 back to the collection and settling tank 10.

The system 100 furthermore includes, downstream of the pressure filter subsystem 60 in the illustrated embodiment, an ultraviolet (UV) light filter 76, a device 80 for adding chlorine, and a treatment tank 90 for adjusting the pH level prior to release of the treated effluent grey water 104 from the system 100. The additional devices, the UV light filter 76, the chlorine adding device 80, and pH-level treatment tank 90 are optional in various embodiments depending on the quality requirements for using the grey water as cleaning water in and around animal stables or whether the grey water is to be drained in open water. In such cases it may be necessary to add these extra devices to the system 100 and corresponding steps to the overall process facilitated thereby.

Figure 2:
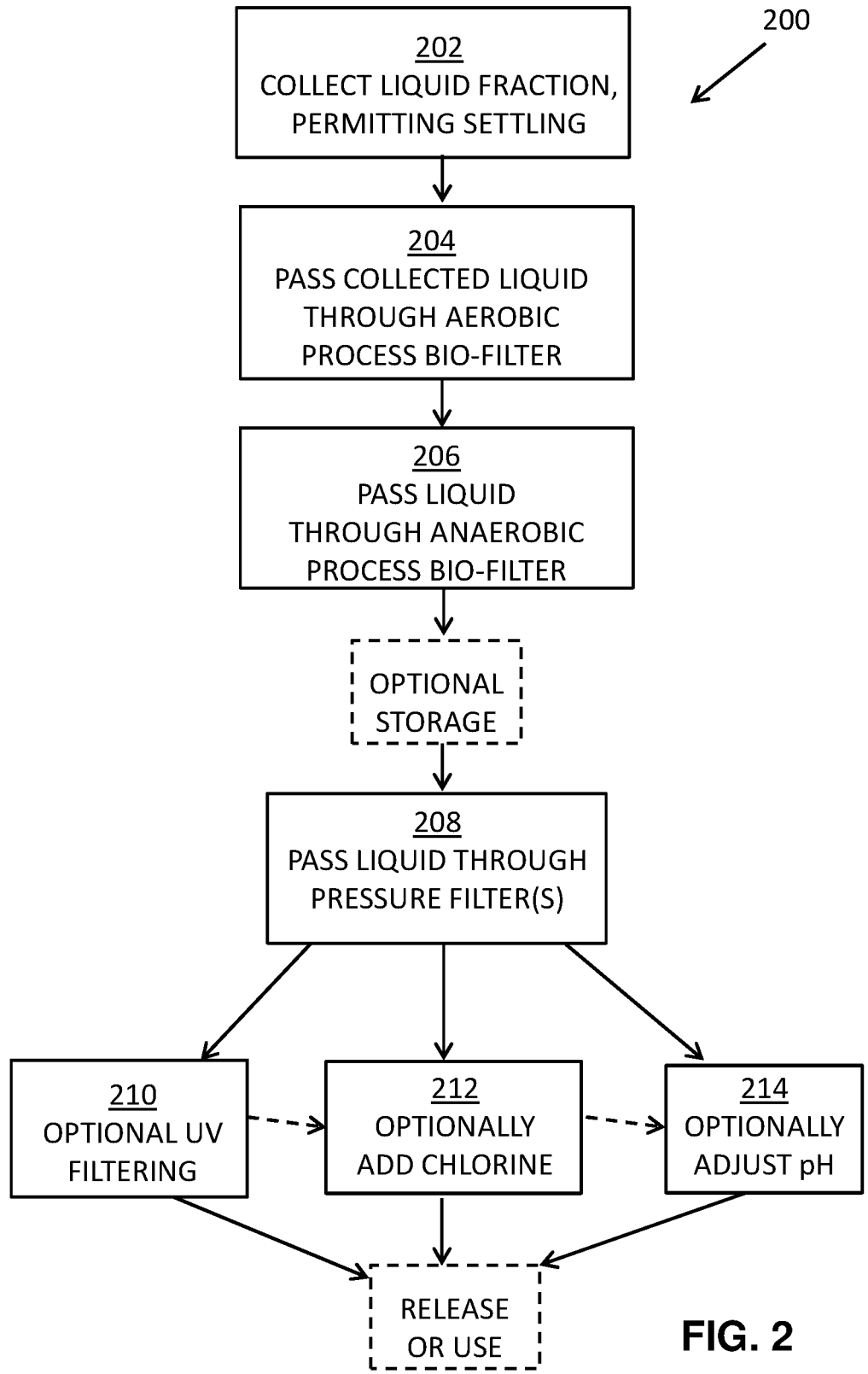
FIG. 2 is a flow chart representing a method, according to at least one embodiment, for obtaining grey water from a liquid fraction of human or animal feces.

Facilitated for example by the system 100, in at least one embodiment, a method 200 for obtaining grey water from a liquid fraction of human or animal feces includes the purification of the liquid fraction using a biological filtration process. The method provides a stepwise approach to reducing the ammonia content of the liquid fraction. As represented in FIG. 2, after separation of dry and liquid portions, the method 200 includes, in step 202 the liquid fraction is stored in a collection and settling tank prior to a biological filtration process. Step 202 may be facilitated, for example, by the collection and settling tank 10 of FIG. 1.

In step 204, the collected liquid fraction is passed through an aerobic first bio-filter over porous granules. The granules may have a microbic culture by which the liquid is treated. In step 206, the liquid is passed through an anaerobic second bio-filter in which the liquid is further treated. Optionally the method includes backwashing for both bio-filters via a backwashing system. Steps 204 and 206 and the optional storage of FIG. 2, in the illustrated or other order, may be facilitated for example by the bio-filter subsystem 30 and collecting tank 44 of FIG. 1.

In step 208, the liquid is passed through pressure filters with the granules. Optionally the method includes backwashing for the pressure filters. The liquid may be stored in a tank after step 206 and before step 208. For example, step 208 may be facilitated for example by the pressure filter subsystem 60 of FIG. 1.

In additional optional steps that may be applied sequentially in any order, or may be applied individually or in any combination, the method 200 may further include, for example after step 208, a step 210 of UV light filtering, a step 212 of adding chlorine, and a step 214 of pH-level adjusting. For example, steps 210, 212 and 214 may be facilitated for example by the UV light filter 76, the chlorine adding device 80, and pH-level treatment tank 90 of FIG. 1.

Steps in FIG. 2 described as potentially facilitated by particular referenced elements of FIG. 1 are not necessarily limited to being practiced by the referenced elements. However, descriptions of FIGS. 1 and 2 should be taken as cumulative, such that the steps of FIG. 2 can be further described according to descriptions of the referenced elements of FIG. 1.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A method for obtaining grey water from a liquid fraction of human or animal excreta, the method comprising:
   passing the liquid fraction from a tank to a first vessel;
   reducing, in the first vessel by an aerobic biological process, an ammonia content of the liquid fraction in a first porous medium in which the ammonia content is at least in part decomposed into at least one byproduct;
   reducing, by an anaerobic process, the at least one byproduct in a second porous medium in which the at least one byproduct is at least in part decomposed into nitrogen; and
   backwashing by aeration the first porous medium thereby recirculating the liquid fraction from the first vessel to the tank,
   wherein an air pressure applied to backwash the first porous medium by aeration is increased relative to an air pressure applied to reduce the ammonia content by the aerobic biological process.

2. The method according to claim 1, wherein:
   the first porous medium comprises granules of a first mineral; and
   the second porous medium comprises granules of a second mineral.

3. The method according to claim 2, wherein at least one of the first and second mineral comprises a zeolite.

4. The method according to claim 3, wherein the zeolite comprises clinoptilolite or mordenite.

5. The method according to claim 1, wherein reducing the ammonia content by an aerobic biological process comprises using bacteria of the nitrosomonas family.

6. The method according to claim 1, wherein the at least one byproduct comprises at least one of nitrates and nitrites.

7. The method according to claim 1, wherein reducing the byproducts by an anaerobic process comprises using bacteria of the nitrobacter family.

8. The method of claim 1, further comprising, prior to reducing the ammonia content of the liquid fraction in the first porous medium, growing a microbic culture in the first porous medium.

9. The method according to claim 8, wherein growing a microbic culture in the first porous medium comprises growing the microbic culture in the first porous medium using a preliminary quantity of the liquid fraction.

10. The method according to claim 1, wherein at least one of the first porous medium and second porous medium comprises porous granules selected from a group consisting of volcanic rock, and zeolite granules of the clinoptilolite or mordenite type.

11. The method according to claim 10, in which the porous granules have a particle size with an average diameter ranging between 10 mm and 30 mm.

12. The method according to claim 1, further comprising, after reducing the ammonia content of the liquid fraction, filtering the liquid fraction thereby removing particles larger than a predetermined size.

13. The method according to claim 12, wherein removing particles larger than a predetermined size comprises removing particles larger than one micrometer.

14. The method according to claim 12, wherein removing particles comprises removing bacteria.

15. The method according to claim 1, further comprising, after reducing the ammonia content of the liquid fraction, reducing a heavy metal content from the liquid fraction by ion-exchange.

16. The method according to claim 1, further comprising, after reducing the ammonia content of the liquid fraction, reducing at least one of oil and fat content of the liquid fraction by adsorption.

17. The method of claim 1, wherein recirculating the liquid fraction from the first vessel to the tank comprises flowing the recirculating liquid fraction downward to below the first porous medium in route to the tank.

18. A method for obtaining grey water from a liquid fraction of human or animal excreta, the method comprising:
    passing the liquid fraction from a tank to a first vessel;
    reducing, in the first vessel by an aerobic biological process, an ammonia content of the liquid fraction in a first porous medium in which the ammonia content is at least in part decomposed into at least one byproduct;
    reducing, by an anaerobic process, the at least one byproduct in a second porous medium in which the at least one byproduct is at least in part decomposed into nitrogen; and
    backwashing by aeration the first porous medium thereby recirculating the liquid fraction from the first vessel to the tank, wherein:
    the first porous medium comprises granules of a first mineral;
    the second porous medium comprises granules of a second mineral; and
    an air pressure applied to backwash the first porous medium by aeration is increased relative to an air pressure applied to reduce the ammonia content by the aerobic biological process.

19. A system for obtaining grey water from a liquid fraction of human or animal excreta, the system comprising:
    a tank for collecting the liquid fraction;
    a first bio-filter for reducing an ammonia content of the liquid fraction, the first bio-filter comprising a first vessel for receiving the liquid fraction from the tank and a first porous medium in which the ammonia content is at least in part decomposed by an aerobic process into at least one byproduct;
    a second bio-filter for reducing the at least one byproduct, the second bio-filter comprising a second vessel and a second porous medium in which the at least one byproduct is at least in part decomposed by an anaerobic process into nitrogen; and
    at least one aeration supply element for backwashing, by aeration, the first porous medium thereby recirculating the liquid fraction from the first vessel to the tank, wherein an air pressure applied to backwash the first porous medium by aeration is increased relative to an air pressure applied to reduce the ammonia content.

20. The system of claim 19, wherein recirculating the liquid fraction from the first vessel to the tank comprises flowing the recirculating liquid fraction downward to below the first porous medium in route to the tank.

* * * * *